United States Patent [19]

Vandevelde et al.

[11] Patent Number: 5,585,367

[45] Date of Patent: *Dec. 17, 1996

[54] METHOD OF TREATING HUMANS AND ANIMALS INFECTED WITH VIRUSES OF THE RETROVIRUS GROUP

[75] Inventors: Michel Vandevelde; Hélène Margery, both of Bierges, Belgium

[73] Assignee: Previsan S.A., Luxembourg, Luxembourg

[*] Notice: The portion of the term of this patent subsequent to Mar. 21, 2012, has been disclaimed.

[21] Appl. No.: 406,143

[22] Filed: Mar. 20, 1995

Related U.S. Application Data

[63] Continuation-in-part of Ser. No. 947,090, Sep. 17, 1992, Pat. No. 5,399,555, which is a continuation of Ser. No. 568,868, Aug. 17, 1990, abandoned.

[30] Foreign Application Priority Data

Apr. 19, 1990 [BE] Belgium ............................... 09000435

[51] Int. Cl.$^6$ ................................................. A61K 31/655
[52] U.S. Cl. ..................................................... 514/150
[58] Field of Search ..................................... 514/150

[56] References Cited

U.S. PATENT DOCUMENTS

| Re. 24,960 | 4/1961 | Urbschat et al. | 167/30 |
|---|---|---|---|
| 3,225,026 | 12/1965 | Huibers et al. | 260/192 |
| 3,325,436 | 6/1967 | Prindle et al. | 260/29.7 |
| 3,637,650 | 1/1972 | Doering | 260/192 |
| 3,684,713 | 8/1972 | Piccolini | 252/47.5 |
| 5,399,555 | 3/1995 | Vandevelde et al. | 514/150 |
| 5,468,469 | 11/1995 | Aszalos et al. | 514/150 |

FOREIGN PATENT DOCUMENTS

| 0196185 | 10/1986 | European Pat. Off. . |
| 0240098 | 10/1987 | European Pat. Off. . |
| 0285357 | 10/1988 | European Pat. Off. . |
| 0307914 | 3/1989 | European Pat. Off. . |
| 2056874 | 5/1971 | France . |
| 2612515 | 9/1988 | France . |
| 9001935 | 3/1990 | WIPO . |

OTHER PUBLICATIONS

Oser et al., "Studies of the Safety of Azodicarbonamide as as Flour Maturing Agent"; Toxicology and Applied Pharmacology; vol. 7, pp. 445–472; 1965.
S. S. Block; "Disinfection, Sterilization and Preservation" Lea & Febiger; 3rd Ed.; pp. 172–179; 1983; Philadelphia.
Sies et al.; "Hepatic Calcium Beflux During Cytochrome P-450-Dependent Drug Oxidations at the Endoplasmic Reticulum in Intact Liver"; Proc. Natl. Acad. Sci. USA; vol. 78; No. 6 pp. 3358–3362; Jun. 1981.
Edited by Reynolds; "Disinfectants and Antispetics"; Martindale The Extra Pharmacopoeia; The Pharmaceutical Press; London; 1982, p. 558—Chloroazodin.
Jentsch et al.; "Inhibition of Human Immunodeficiency Virus Type I Reverse Transcriptase by Suramin–Related Compounds"; J. Gen. Virol.; pp. 2183–2192; May 1987.

Kumler; "The Dipole Moments Ultraviolet Spectra of AZO-BIS-(Chloroformamidine) And AZO-BIS-(Nitroformamidine)"; Journal of the American Chemical Society, vol. 75; pp. 3092–3093; 1953.
Resnick et al.; "Stability and Inactivation of HTLV-111/LAV Under Clinical and Laboratory Environments"; JAMA; vol. 255, No. 14; p. 1887–1891; Apr. 11, 1986.
Spire et al.; "Inactivation of Lympha Denopathy Associated Virus By Chemical Disinfectants"; The Lancet; pp. 899–901; Oct. 20, 1984.
Martin et al.; "Disinfection and Inactivation of the Human T Lymphotropic Virus Type III/Lymphadenopathy–Associated Virus" The Journal of Infectious Disease; vol. 152; 400–403; Aug. 1985.
Kosower et al.; "Diamide. A New Reagent for the Intracellular Oxidation of Glutatione to the Disulfide"; Biochemical and Biophysical Research Communication; vol. 37, No. 4, pp. 593–590 1969.
Schmelkes et al.; "N,N'–Dichloroazodicarbonamidine (Azochloramid) An N–Chloro Derivative Oxidant in an . . . " Chemical Society; vol. 56 pp. 1610–1612; 1934.
Hanson, et al.; "Chemical Inactivation of HIV on Surfaces"; BMJ, vol. 298; p. 862–864; Apr. 1, 1984.
Huraux et al.; "Virologie"; Flammarion Medecine Sciences pp. 305; 1985.
Schulhafer et al.; "Acouire Immunodeficiency Syndrome: Molecular Biology and its Therapeutic Intervention (Review)"; In Vivo 3 (2); pp. 61–78; (1989).

(List continued on next page.)

*Primary Examiner*—Russell Travers
*Attorney, Agent, or Firm*—Watson Cole Stevens Davis, P.L.L.C.

[57] ABSTRACT

Compositions useful in methods of treating humans and animals infected with viruses of the retrovirus group contain azoic compounds of the general formula

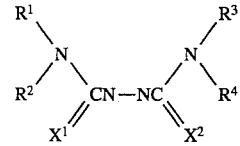

wherein $R^1$, $R^2$, $R^3$ and $R^4$ are indentical or different and each represents an atom of hydrogen or an aliphatic or aromatic hydrocarbon radical comprising from 1 to 6 carbon atoms, $R^1$ and $R^2$ may be bonded together to form a heterocyclic ring with their adjacent nitrogen atom, and $R^3$ and $R^4$ may be bonded together to form a heterocyclic ring with their adjacent nitrogen atom; $X^1$ and $X^2$ are indentical or different and each represents an oxygen atom or an $NR^5$ group, wherein $R^5$ is a hydrogen atom, an aliphatic or aromatic hydrocarbon radical comprising from 1 to 6 carbon atoms, or a nitro group; and wherein when two $NR^5$ groups are simultaneously present each $R^5$ may be indentical to or different from the other.

28 Claims, 1 Drawing Sheet

OTHER PUBLICATIONS

Miller et al.; "Genital Mucosal Transmission of Simian Immunode–Ficiency Virus: Animal Model for Heterosexual Transmission of Journal of Virology"; pp. 4277–4284; Oct. 1989.

D'Agay et al.; "Syndrome Immuno Deficitaireacquis"; Doin Editein $2^e$ edition; pp. 183–184; 1986.

Walker et al. "Inhibition of human immunodeficiency virus . . ." Proc. Nat'l. Acad. Sci. USA, vol. 84 pp. 8320–8124, Nov. 1987.

LePage et al. "posinatal Transmission of HIV from Mother to Child" The Lancet, Aug. 15, 1987 p. 400.

Merck Index p. 132 definition of Azodicarbonamide, 1983.

Hanson, et al.; "Chemical Inactivation of HIV on Surfaces"; BMJ, vol. 298; pp. 862–864; Apr. 1, 1989.

"The Chemistry of Amidines and Imidates", edited by Saul Patal, 1975, John Wiley & Sons, pp. 48–51.

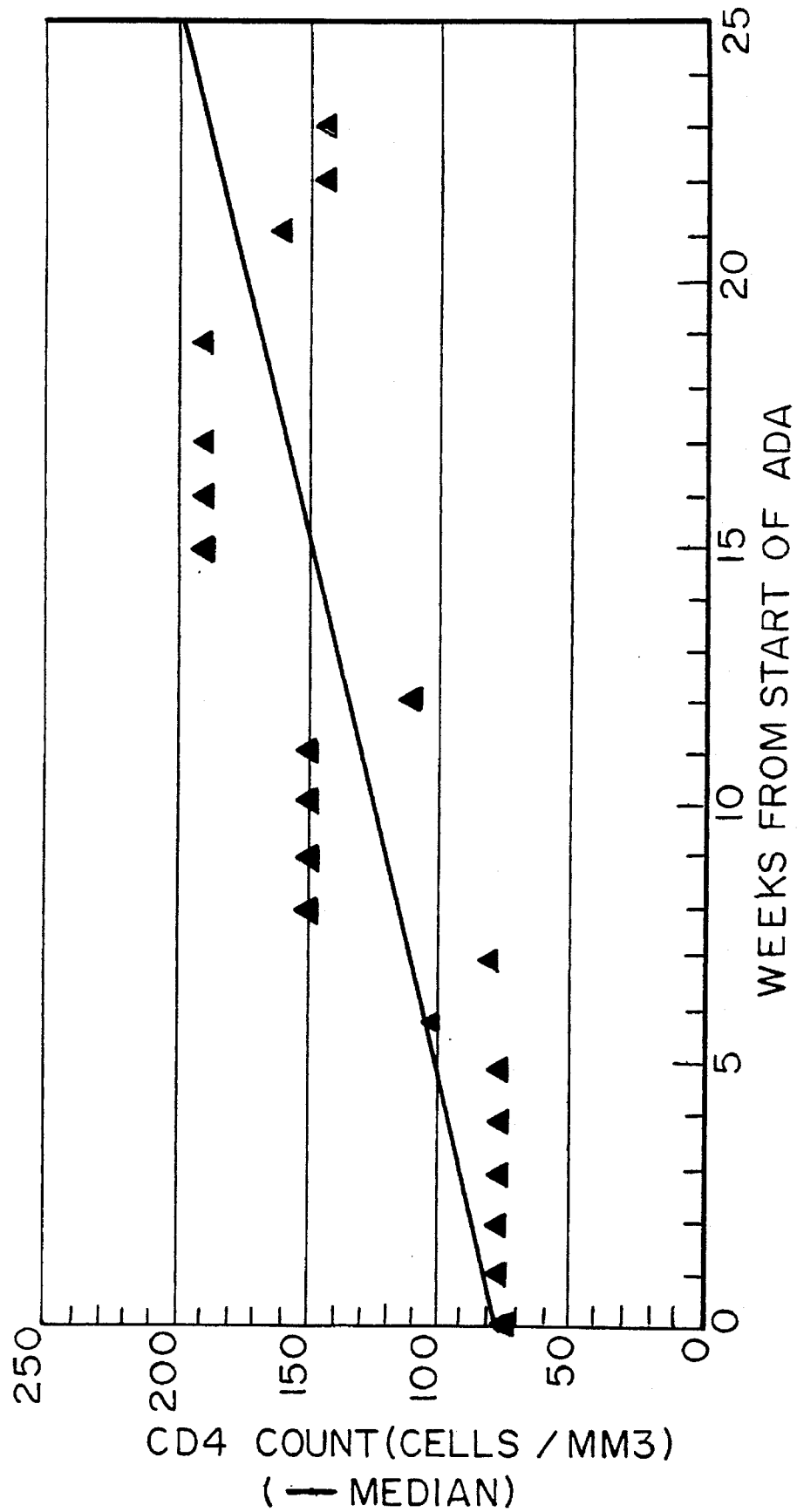

METHOD OF TREATING HUMANS AND ANIMALS INFECTED WITH VIRUSES OF THE RETROVIRUS GROUP

CROSS REFERENCE TO RELATED APPLICATIONS

The present application is a continuation-in-part of U.S. application Ser. No. 07/947,090, filed Sep. 17, 1992, issued as U.S. Pat. No. 5,399,555 on Mar. 21, 1995; which in turn is a continuation of U.S. application Ser. No. 07/568,868, filed Aug. 17, 1990, now abandoned.

FIELD OF THE INVENTION

The present invention relates to azoic derivatives and to pharmaceutical and disinfectant compositions containing these derivatives.

The present invention also relates to methods of treating humans and animals infected with viruses of the retroviruses group, by using the derivatives and compositions.

BACKGROUND OF THE INVENTION

The retroviruses are defined according to the invention as viruses wherein the genetic material carried on a chain of ribonucleic acid is transcribed inside a target cell of desoxyribonucleic acid by means of an enzyme called reverse transcriptase.

These viruses are responsible for pathologies in the vegetal and animal worlds. A non-exhaustive list of said viruses is to be found in J. M. HURAUX et al., Virologie, Flammarion Medecine-Science, 1985, Paris.

When the integration stage in the target cell chromosomes has been reached, the recovery likelihoods (return to the previous condition) are low. As a matter of fact, these viruses infect cell series of various types and no drug able to extract the viral genetic material from infected cells seems to be probable at the present time.

Besides, these viruses have mutation properties and they are screened by animal pools which allow them to occur as new antigenic forms (by use of cellular fragments of the host cell, for example), which causes the vaccination to be complex.

Today only one treatment is known which extends the survival of the patients, however not allowing a cure. This treatment comprises administration of 3'-azido-3'-desoxythymidine (see EP-A196185). This substance acts by reverse transcriptase inhibition.

Other substances are known as inhibiting replication of viruses HIV through their action on the reverse transcriptase. Some didesoxynucleotides (see EP-A-307914) may be, for example, cited.

It has also been found that some substances have as an effect to block the penetration of the viruses into the cells. As substances having this effect, it may be cited for example oligo-saccharides or polysaccharides (see EP-A-240098) or also castonospermine (B. D. WALKER, Inhibition of human Immunodeficiency virus suncytium formation and virus replication by castonospermine, Proc. Nail. Acad. Sci. USA, vol. 84, p. 8120–8124, Nov. 1987).

According to these treatments, it may be hoped that the virus having infected a patient will not follow its development and its propagation. However, the patient does not return to this condition before the affection because the provirus is not affected and it subsists inside the cell which has been previously attacked. The treatment is thus palliative and not curative.

This kind of treatment has the important danger to allow resistance of viruses to compounds to appear. It seems already established that the virus becomes resistant to 3'-azido-3'-desoxythymidine after a more or less long term, in particular after about 12 to 18 months (SCHULHAFER E. et al., Acquired immuno-deficiency syndrome . . . , In Vivo 3(2):61–78 (1989)).

Finally, it has already been considered to use, as a drug against retroviruses, some benzidine derivatives which bear amongst others azoic groups (see FR-A-2612515). However, in this document there is only a simple affirmation concerning the activity of these compounds.

The transmission way of the viruses have been determined in case of a direct blood contact and contact through wounds by infected material. The risk of a transmission from infected objects and particularly medical material is not to be neglected.

On the other hand, the sexual transmission and the transmission to children via infected mother's milk are also established, which shows that the passage of infecting particles through sound mucosas is possible. (P. LEPAGE et al., Postnatal Transmission of HIV from Mother to Child, The Lancet, Aug. 15, 1987 p. 400; C. J. MILLER et al., Genital Mucosal Transmission of Simian Immunodeficiency Virus, Journal of Virology, Oct. 1989, pp. 4277–4284).

The existence of a virus, inoculation by way of a simple contact, i.e. through skin or mucosa, seems more and more likely. According to the opinion of some searchers, the inoculated viruses would seem to go through a replication phase during which they remain in the area of the mucosa or skin of the carrier. This phase could continue for several months. It would be in the second phase only that the viruses and/or the constituents thereof would spread from the mucosa. (R. ZITTOUN, Syndrome Immuno Déficitaire Acquis, Doins Editeurs, Paris, 1986, p. 183–184).

Thus for the eradication of the disease, it is appeared as necessary to prepare molecules able to disinfect inanimated surfaces and objects, as well as materials and products which come into contact with mucosa and skin. It is appeared as essential to impede as far as possible the retrovirus transmission from a carrier to a healthy person.

Compositions and a method for disinfecting, which use natural or synthetic oliosaccharides or polysaccharides having at least one S-oxoacid group, are already known (see EP-A-285357). However, from the Examples, it results clearly that, even if these compositions are active against the retroviruses, a part of the treated viruses always subsist, with the enormous risk to see after a term the generation of a still more dangerous resistant virus population.

In an international patent application WO-A-90/01935, products are already provided, which are able to come locally into contact with skin, mucosas or body secretions, these products comprising an agent active against the viruses of the retrovirus group, for example sodium suramine, as well as some complex azoic derivatives such as pyridium, neotropine, Congo red, trypan blue, trypan red and trypan violet.

The action of usual chemical disinfectants, such as ethanol, glutaraldehyde, sodium hypochlorite, formalin, β-propiolactone, methylated spirit amongst others, has been examined against retroviruses. (V. B. SPIRE et al., Inactivation of Lymphadenopathy associated virus by chemical disinfectants, The Lancet, Oct. 20, 1984, pp. 899–901; L. RESNICK et al., Stability and inactivation of HTLV-III/

LAV under clinical and laboratory environments, JAMA, Apr. 11, 1986, Volume 255, No. 14 ; L. S. MARTIN et al., Disinfection and inactivation of the human T lymphotropic Virus type III/lymphadenopathy-associated virus, The Journal of Infectious Diseases, Vol. 152, No. 2, Aug. 1985; P. J. V. HANSON et al., Chemical inactivation of HIV on surfaces, Br. Med. J., 1989, 198:862–4).

It results from these assays that most of tile disinfectants used in hospitals are inefficacious or not very efficient against retroviruses HIV, and consequently potentially dangerous. Those which are the most efficient require rather long contact times, sometimes 10 minutes and more, which is concretely difficult to apply for cleaning grounds, tables, for example. Moreover, some of said disinfectants seem to lose their effectiveness in the presence of proteinaceous materials or are not of application if they must come into contact with the skin or the mucosa of a living body, due to their chemical agressivity or their cellular toxicity.

SUMMARY OF THE INVENTION

Consequently, the present invention has for its object to provide an active agent against the viruses, particularly of the retrovirus group, in particular the human immunodeficiency viruses HIV, this agent being able to be radically active on said viruses, preferably with a complete removal of the latter, while maintaining its activity at very low concentrations. Advantageolusly, said agent will maintain its active power within a cellular medium, an aqueous medium as well as in the presence of organic, particularly proteinaceous materials. Its toxicity will preferably be low. According to a preferred embodiment, the virucidal action will be very rapid against the viruses HIV.

The invention has also for its object to provide a pharmaceutical composition allowing the treatment or prophylaxis of viral diseases.

The invention has also for its object to prepare a composition for disinfecting inanimate objects against viruses.

It is obvious that, according to its applications, either as active substance in a pharmaceutical composition, or as disinfecting agent in a cleaning product, a cosmetical composition or other products of this kind, the active agent will have to meet different requirements concerning solubility, toxicity or stability. It will be the same if application of the pharmaceutical composition must be made orally, parenterally, intravenously, topically or following another administration way, or if the disinfection concerns inanimate objects such as instruments or grounds, or on the contrary organic wastes or liquids to be absorbed.

Suprisingly, it has been found that some azoic compounds are able to particularly effectively and radically play the part of the searched active agent.

DETAILED DESCRIPTION OF THE INVENTION

To solve the raised problems, it has been provided, according to the invention, azoic derivatives having the general formula:

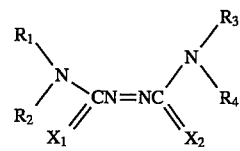
(1)

wherein $R_1$ to $R_4$ are identical or different and each represent an atom of hydrogen or halogen, or a substituted or not, aliphatic or aromatic hydrocarbon radical, comprising from 1 to 6 carbon atoms; $X_1$ and $X_2$ are identical or different and each represent an oxygen atom or a $NR_5$ group, in which $R_5$ is a hydrogen or halogen atom, an aliphatic or aromatic hydrocarbon radical comprising from 1 to 6 carbon atoms or a nitro group; $R_5$ when two $NR_5$ groups are simultaneously present, may have an identical or different meaning in each of said groups, and $R_5$ having a meaning other than an atom of chlorine simultaneously in both $NR_5$ groups when $R_1$ to $R_4$ represent hydrogen, as well as their salts, esters and isomers, as therapeutically active substances. According to one embodiment, $R^1$ and $R^2$ are bonded together and form a heterocyclic ring with their adjacent nitrogen atom. According to one embodiment, $R^3$ and R4 are bonded together and form a heterocyclic ring with their adjacent nitrogen atom. According to yet another embodiment, $R^1$ and $R^2$ are bonded together and form a heterocyclic ring with their adjacent nitrogen atom and $R^3$ and R4 are bonded together and form a heterocyclic ring with their adjacent nitrogen atom.

According to the invention, in these derivatives, $R_1$ to $R_5$ may advantageously represent independently a lower aliphatic hydrocarbon radical, in particular a methyl, ethyl, propyl or butyl group. Benzyl groups may also be provided. In the compounds according to formula 1, the halogen atoms are in particular those of chlorine, bromine, iodine and fluorine.

As azoic derivatives according to the invention, one may in particular consider 1.1'-azobisdimethylformamide, 1.1'-azobisformamidine, 1.1'-azobisdimethylformamide, 1.1'-azobisnitroformamidine. Particular active substances used in the compositions of the present invention include azobisformamide, 1,1'-azobisformamide, and 1,1'-(azodicarbonyl)dipiperidine.

Single doses of between 7 and 140 mg per kg body weight are tolerable and effective in increasing CD4 cell count and enabling weight gain without causing diarrhea. Single doses of between 7 and 140 mg per kg body weight 1,1'-azobisformamide (ADA) have proven tolerable and effective. The total amount per single dose can vary and may fall within the range of 500 and 12,000 mg ADA per single dose.

Administered three times a day, individual doses may range from 20 mg per kg body weight or less, to 90 mg per kg body weight or more. The dosage and dosage per kg body weight will vary depending upon a number of factors such as the overall health of the patient, the stage of the disease, and the effective body weight of the patient or volunteer. Total daily dosages of up to 18,000 mg per day may be administered.

Treatments according to the present invention are expected to be effective against HIV and other viruses of the retrovirus group. Treatments using ADA have proven particularly effective, as discussed below.

It has to be understood that the invention is not limited to 1.1'-derivatives and that those in 2.2'-position are also included in the invention, as well as all the isomers and their mixtures.

Preparation of 1.1'-azobisformamidine and 1.1'-azobisformamide has already been carried at the end of the last century by J. THIELE (see The Merck Index, 10 ed., 919, Rahway, 1983; F. C. SCHMELKES et al., N,N'-Dichloroazodicarbonamidine (azochloramide), an N-chloro derivative of the oxidant in an oxidation-reduction system, Journal of American Chemical Society, 56, 1610, 1934). 1.1'-Azobisformamide has been known as an adjuvant in food flour.

1.1'-Azobisdimethylformamide has also been known for a long time due to its intracellular oxidising action on human blood cell glutathione (N. S. KOSOWER et al., Diamide, a new reagent for the intracellular oxidation of glutathione to the disulfide, Biochemical and Biophysical Research Communications, vol. 37, No. 4, 1969). 1.1'-Azobisnitroformamidine has also been known from a long time. (W. D. KUMLER, The Dipole Moments, Ultraviolet spectra and structure of azo-bis-(chloroformamidine) and azo-bis-(nitroformamidine), Journal of American Chemical Society, 75, 3092, 1953). It is clearly apparent from the documents of this state of the art that it has been fully unexpected to obtain the searched effect from these relatively simple substances which are unexpensive to manufacture and known for a very long time.

A still more unexpected effect has been seen. It is appeared that some derivatives have a selective toxicity against cells infected by HIV virus, while the Supt-1 cells and the lymphocyte cells of the human body are not or only a little altered by the tested compounds. These observations have allowed to consider the possibility of a chemiotherapy which selectively destroys the infected cells while maintaining the sound cells of the patient. One may thus consider a recovery to the previous condition of the treated patient, i.e. a cure of the latter.

According to the invention, it is thus provided a pharmaceutical composition comprising, as active substance, at least one azoic derivative having the general formula of claim 1 or a salt, ester or isomer which is pharmaceutically acceptable of said derivatives, and at least one pharmaceutically compatible excipient, as well as if necessary one or more pharmaceutically current adjuvants. This composition may be administered as any form, orally or sublingually, rectally or vaginally, by injection or perfusion, topically, transcutaneously or transmucosally, or by any other current form in therapeutical or veterinary medecine. The excipient and possible current adjuvants are selected according to the selected administration way. Advantageously, preservation or solubilization agents, pH neutrality agents, isotonicity agents, buffer agents or other agents may be added to the composition.

The selected excipient or vehicle can be solid or liquid. The composition will be at the option as a powder, ointment, tablets, capsules, aerosols, liquid to be injected and the like.

Also some formulas which release the active substance with late effect can also be provided.

According to an advantageous embodiment of the invention, the pharmaceutical composition according to the invention comprises a disinfectant as a supplement. As a matter of fact, in addition to the curative effect of the composition, it may be advantageous for the virus carrier that the composition defends him against external aggressions which, while stimulating his immunitary defence system, promote the proliferation of the HIV viruses that he carries.

Also according to the invention, the same azoic derivatives having the above-mentioned formula are provided as active substances to combat, on and/or in inanimate objects, with the viruses, in particular of the retrovirus groups, more particularly the HIV human immunodeficiency viruses.

According to the invention, it is also provided compositions to disinfect inanimate objects, containing at least one of these active azoic derivatives as well as a suitable vehicle. As vehicle, one may advantageously provide water or any other suitable solvent in which the active agent is in solution. Other current disinfectant or adjuvant agents can be if necessary provided in supplement.

According to the invention, use of the active azoic derivatives or of above-mentioned disinfection compositions is made for the disinfection of inanimate object against the viruses, in particular the retrovirus group, more particularly HIV human immunodeficiency viruses.

As inanimate objects to be disinfected, use of the present invention can be made, lot example with:

plastic, rubber or textile sanitary materials: wadding, absorbent cotton-wool, gauze, bandages, toilet paper, packing films, and the like.

medical, veterinary or dentist instruments and apparatuses: syringes, cannulas, sounds, clips, scissors, stomachal washing kits, surgical tables, basins, and the like.

medical, veterinary or dentist clothes: gloves, dresses, towels, and the like.

cosmetology instruments: material and equipment for hairdresser, manicurist, chiropodist, beautician, and the like.

objects requiring a handling in the alimentary field: feeding-bottles, pans, bottles or cans, in particular for beverages, and the like.

sanitary vehicles: ambulances, rolling tables, and the like.

ground or wall surfaces: quarters or blocks, particularly in hospitals, and the like.

sanitary and hygienic apparatuses: wash-hand basins, urinal vessels, dishes, bath-tubs, and the like.

beverages: water necessary for beverages, milk, and the like.

water for swimming pools.

The disinfection of excrements, wastes of analysis laboratories and particularly of samples taken off from a human or animal body, for example lot an analysis, can be provided.

According to the invention, some cosmetic compositions can advantageously be provided in order to include also at least an active azoic derivative of the invention. Obviously in this case, various usual carriers and additives in this field can be applied.

A particular use of an active agent or of an active composition according to the invention can be provided in or on products which can come into contact with the skin or the mucosa of a human or animal body, which optionally is a virus carrier. In or on some of said products, such as physician or dentist gloves, pessaries, contraceptive sheaths, and the like, the active agent or composition can in addition to its disinfecting action form a barrier medium for the transmission of retroviruses from a carrier to a healthy person. For example, it is possible to lubricate a contraceptive rubber sheath with a petrolatum including an active agent according to the invention. For physician gloves, it is also possible to provide two rubber films between which is for example located an amylase amylopectin powder including an active agent according to the invention. In the last case, the disinfecting powder to be used as barrier is thus not in direct contact with the skin.

The disinfection composition according to the invention may also optionally contain a disinfectant agent as a supplement, preferably with a wide spectrum of germicidal action. The so obtained composition has thus an appreciable defense against the presence of pathogenic or allogenic agents, other than retroviruses HIV.

This last property is very important not only due to the important disinfection action such as obtained, but also because it can be useful for the virus carrier himself. As a matter of fact, the latter must avoid as much as possible any activation of his lymphocytar cells. Such an activation, for the HIV carrier, has as an effect the replication of the virus and the proliferation thereof in his cells. A HIV carrier must advantageously follow hygienic life habits in order to avoid at the maximum any risk of infected cell activation and consequently an immunitary reaction of his organism.

By the use of agents and compositions according to the invention, the virus carrier has the possibility to disinfect himself, but also additionally to obtain a protection against immunitary reactions from another source.

BRIEF DESCRIPTION OF THE DRAWINGS

FIG. 1 shows media values of all CD4 lymphocyte counts measured in patients.

The invention will now be illustrated in a more detailed manner by means of some non-limiting examples.

EXAMPLE 1

| Tablets | |
|---|---|
| 1.1'-azobisdimethylformamide | 200–300 mgr |
| Microcristalline cellulose (Avicel PH 101) | 60 mgr |
| Povidone BP | 15 mgr |
| Sodium starch glycolate | 20 mgr |
| Magnesium stearate | 5 mgr |
| lactose, q.s. for | 500 mgr |

EXAMPLE 2

| Capsules | |
|---|---|
| 1.1'-azobisformamide | 400–600 mgr |
| Microcrystalline cellulose (Avicel) for one capsule | 50 mgr |

EXAMPLE 3

| Long-release composition (6 to 8 hours) | |
|---|---|
| 1.1'azobisdimethylformamaide | 400–600 mgr |
| Hydroxypropyl methyl cellulose | 111 mgr |
| Lactose | 53 mgr |
| Povidone BP | 28 mgr |
| Magnesium stearate | 7 mgr |

First, hydroxypropyl methyl cellulose is mixed with 1.1'-azobisdimethylformamide, then the other components are added.

EXAMPLE 4

| Injectables | |
|---|---|
| 1.1'-azobisformamide | 10–30 mgr |
| Hydrochloric acid | 0.1 M |
| Sodium hydroxide | 0.1 M | pH is adjusted to a value of 4 to 7 by means of either the acid or the base, the product is hot dissolved and filtration is made on sterile micropore. The liquid is then poured into brown sterile ampoules.

EXAMPLE 5

| Injectables | |
|---|---|
| 1.1'-azobisformamidine | 50–150 mgr |
| Benzyl alcohol | 10 mgr |
| Glycofurol | 75 mgr |
| Water for injection | 3 ml |

The product is prepared by dissolution of the active substance in glycofurol, then mixing the so obtained solution with filtered water and benzyl alcohol. The whole is poured into a sterile brown ampoule.

EXAMPLE 6

| Injectables by intravenous way | |
|---|---|
| 1.1'-azobisnitroformamidine | 50–150 mgr |

Sterile water without pyrogen is added to this component, this water being buffered by a phosphate buffer at pH 7, in order to obtain 27 ml.

EXAMPLE 7

Suppository

To 150–250 gr of micronized powder of 1.1'-azobisformamidine, 2 gr of glycerin are added in order to form a suppository.

Experimental tests have been made by the laboratory of Institut Pasteur of Brabant, Belgium, in order to examine the efficiency of the azoic derivatives according to the invention.,

EXAMPLE 8

Starting Materials of the Test 1.1'-azobisformamidine of a purity level of 98%. The purity has been examined by a carbon-hydrogen test, a supernatent of cell cultures (Molt-3) which continuously produce HIV-1 viruses, The used viral supernatent has a reverse transcriptase activity of $1\times10^6$ cpm/ml, cells of a continue human T line of $T_4$ phenotype (Supt-1) cultivated in a RPMI medium additionally supplied with 10% of foetal calf serum and 1% of glutamine, The effectiveness of 1.1'-azobisformamidine has been investigated on two aspects:

its toxicity against sound cells its action on the infectious power of HIV-1 viruses for the Supt-1 line.

(a) Examination of the Toxicity against Sound Cells

The cellular mortality has been determined by exclusion with trypan blue. To dilutions of 1/500, 1/1500 and 1/3000, 1.1'-azobisformamidine does not decrease the cellular viability of Supt-1 cells.

(b) Examination of the Infectious Power

Vital preparations of HIV-1 of high titer are incubated in the presence of dilutions of 1.1'-azobisformamidine of 1/500, 1/1500 and 1/3000 and for different incubation periods: 1 minute, 10 minutes and 30 minutes. For the incubation, 0.3 ml of virus concentrate and the active substance are brought together at a double concentration (once for the virus volume and once for the product volume). For 30 minutes at 37° C., the Supt-1 cells are previously treated with 10 μgr/ml of polybren, then they are inoculated with the preparations of treated viruses. As controls, non-inoculated cells and cells inoculated with a non-treated virus preparation are provided.

Then, the infectious power of said preparations is determined, for each cellular passage, the vital production (measure of the expressed p24 antigen) being followed in the solubilized cellular lysates of the examined Supt-1 cells.

The measures of the infectious power of HIV-1 virus after incubation with 1.1'-azobisformamidine appear from the following Table 1, by comparison with a non-infected control and with a control infected by non-treated viruses.

EXAMPLE 9

The starting material for the test differs from that of Example 8 by using 1.1'-azobisdimethylformamide instead of 1.1'-azobisformamidine.
(a) Toxicity Examination
At dilutions at 1/500, 1/1500 and 1/3000, the 1.1'-azobisdimethylformamide does not decrease the cellular viability of the Supt-1 cells.
(b) Examination of the Infectious Power
One proceeds in the same way as in Example 8b. The measures of the infectious power of the HIV-1 virus after incubation with 1.1'-azobisdimethylformamide appear from the following Table I.

TABLE 1

Measure of the infectious power of tthe HIV-1 on the 14th day after inoculation of Supt-1 cells.

| Active substance (dilution) | Duration of the treatment of the viruses | |
|---|---|---|
| 1.1'-Azobisformamidine | | |
| 1/500 | 1 min | 0.234 ± 0.008 |
| | 10 min | 0.267 ± 0.021 |
| | 30 min | 0.245 ± 0.020 |
| 1/1500 | 1 min | 0.469 ± 0.013 |
| | 10 min | 0.439 ± 0.008 |
| | 30 min | 0.406 ± 0.032 |
| 1/3000 | 1 min | 0.809 ± 0.049 |
| | 10 min | 0.505 ± 0.023 |
| | 30 min | 0.740 ± 0.013 |
| 1.1'-Azobisdimethylformamide | | |
| 1/500 | 1 min | 0.275 ± 0.049 |
| | 10 min | 0.206 ± 0.006 |
| | 30 min | 0.203 ± 0.008 |
| 1.1500 | 1 min | 0.278 ± 0.050 |
| | 10 min | 0.217 ± 0.028 |
| | 30 min | 0.193 ± 0.004 |
| 1/3000 | 1 min | 0.239 ± 0.016 |
| | 10 min | 0.283 ± 0.042 |
| | 30 min | 0.198–0.009 |
| Virus control | | 1.033 ± 0.081 |
| Cell control | | 0.206 ± 0.005 |
| | | (optical density 492 nm). |

It is clearly apparent from this Table that at a dilution of 1/500, 1.1'-azobisformamidine protects the Supt-1 cells after a treatment of the viruses for 1 minute only. 1.1'-azobisdimethylformamide has this effect even at dilutions of 1/3000. For the latter substance, the test has been extended up to the 25th day. The effectiveness of this active substance is maintained for all the dilutions, when the viruses have been treated for 30 mintues.

On the other hand, with a phase-contrast microscope, no cytopathogenic effect was observed for the cells inoculated with virus previously treated with 1.1'-azobisdimethylformamide and 1.1'-azobisformamidine. On the contrary, syncytia appear from the 14th day on after infection with the control viral preparation.

(c) 1.1'-azobisdimethylformamide Has Moreover Been Examined Concerning Its Toxicity Against Cells Infected with Viruses To this end, the cellular mortality has been determined by exclusion with trypan blue.

This examination has been made on Molt-3 cells infected by HTLVIII-B which are producing HIV-1 viruses.

TABLE 2

| Molt-3 cells (HIV-1) | | Number of living cells | Number of dead cells | % of dead cells |
|---|---|---|---|---|
| Control | | 57 | 5 | 8 |
| Cells treated witth 1.1'-azobisdimethylformamide | | | | |
| Dilution | Duration (min.) | | | |
| 1/500 | 1 | 62 | 9 | 12.7 |
| | 10 | 67 | 11 | 14 |
| | 30 | 58 | 12 | 17.1 |
| 1/1500 | 30 | 70 | 15 | 17.6 |
| 1/3000 | 30 | 58 | 12 | 17.1 |

It results very clearly from the Table 2 that the mortality of the infected cells is doubled in the presence of 1.1'-azobisdimethylformamide after 30 minutes of action, even at the dilution of 1/3000, while this molecule shows no toxicity for the human Supt-1 and lymphocyte cellular lines, even after 24 th hours.

EXAMPLE 10

The test material is different from that of Example 9 in that 1.1'-azobisdimethylformamide is dosed at a dilution of 1/100 (10 mgr/ml).

(a) Examination of the Cellular Toxicity Against Normal Cells, Namely Non-Infected Cells (Supt-1 line)

The cellular mortality has been determined by exclusion with trypan blue.

TABLE 3

| Supt-1 cells | Duration (hours) | Number of living cells | Number of dead cells | % of dead cells |
|---|---|---|---|---|
| Controls | 0 | 61 | 19 | 24 |
| | 1 | 57 | 18 | 32 |
| | 5 | 55 | 20 | 36 |
| Cells treated with 1.1'-azobisdimethyl-formamide (dilution 1/100) | 0 | 61 | 21 | 26 |
| | 1 | 63 | 20 | 24 |
| | 5 | 56 | 22 | 28 |

These results are given by ml of culture which was taken off.

It is clearly apparent from the Table that, even at a relatively high concentration, the 1.1'-azobisdimethylformamide has no toxicity against sound Supt-1 cells.

(b) Examination of the Infectious Power of the HIV-1 Virus

One proceeds as in Example 8(b) by treating the viruses for 30 minutes with 1.1'-azobisdimethylformamide at a dilution of 1/1000. After inoculation of Supt-1 cells with this viral preparation, the p24antigens are determined, being expressed by the optical density, after 14, 18 and 21 days.

TABLE 4

| p24 Antigens expressed by optical density | | | |
|---|---|---|---|
| | Day 14 | Day 18 | Day 21 |
| Control cells | 0.125 | 0.126 | 0.168 |
| Control cells infected by HIV | 0.224 | 1.078 | 0.765 |
| Cells + HIV-1 treated by the acive substance | 0.144 | 0.160 | 0,130 |

It is apparent from this experience that the HIV treated with 1.1'-azobisdimethylformamide is not able to infect the sound Supt-1 cells.

(c) Examination of the Integration of the Viral Genome into the Chromosomic DNA of Supt-1 Cells By means of a genetic amplification through a thermostable polymerase, the presence of genes "GAG", "LTR" and "ENV" of the HIV-1 provirus is evidenced. This method is called P.C.R. Polymerase chain Reaction) (Chin-Yih Ou et al., Sciences 239, 295–297, 1988).

Said method is applied for detecting HIV-1 provirus in the genome of Supt-1 cells inoculated with HIV-1 virus incubated with 1.1'-azobisdimethylformamide (dilution 1/100), as described in Example 8

Amplified oligonucleotides, UV visible by means of ethidium bromide appear only in the tubes corresponding to an inoculation with HIV-1 viruses which were not treated with the active substance.

Moreover, after hybridaton with specific $p^{32}$ marked moulds for to the three searched genes, it is possible to conclude that HIV-1 provirus is totally absent within Supt-1 cells which have received inoculates of HIV-1 virion treated with a 1/100 dilution of to the active substance.

It may thus be deducted that this active substance protects the cells against the infection by HIV-1.

EXAMPLE 11

The test material is different from that of Example 8 in that the used substance is 1.1'-azobisformamide dosed at a concentration of 35 mgr/l, i.e. 35 μgr/ml, namely at an extremely low concentration (obtained by the supernatent of a suspension of 0.5 gr/l in RPMI).

(a) Examination of the Cellular Toxicity Against Sound Cells

No toxic effect has been noted for to the Supt-1 cells, even after 24 hours of incubation.

(b) Examination of the Infectious Power

One proceeds as in Example 8(b) with incubation periods of the viruses of 15 minutes 30 minutes, 60 minutes and 120 minutes. No cytopathogenic effect has been observed (no formation of syncytia).

TABLE 5

| p24 Antigens expressed by optical densiy | | | |
|---|---|---|---|
| | Day 14 | Day 18 | Day 21 |
| Control cells | 0.140 | 0.142 | 0.136 |
| Infected conrol cells | 1.014 | 1.510 | 0.730 |
| Cells + HIV-1 treated 15 min. | 0.134 | 0.150 | 0.140 |
| Cells HIV-1 treated 30 min. | 0.152 | 0.170 | 0.146 |
| Cells + HIV-1 treated 60 min. | 0.142 | 0.162 | 0.135 |
| Cells + HIV-1 treated 120 min. | 0.145 | 0.168 | 0.154 |

It can thus be concluded that the 1.1'-azobisformamide protects the cellular cultures against the infectious power of HIV-1.

(c) Examination of the Integration of the Viral Genome into Chromosomic DNA of Supt-1 Cells One proceeds as in Example 11(c). The search of genes "GAG", "LTR" and "ENV" has been made in cellular cultures inoculated with a virus incubated for 15 minutes with the active substance. This search is appeared as being negative, and thus it can be concluded that 1.1'-azobisformamide at the dosage of 35 μgr/ml protects the cells against infection by HIV-1.

EXAMPLE 12

The absence of toxicity of azobisformamide for the humans has already been described by B. L. OSER et al., Studies of the Safety of Azodicarbonamide as a Flour-Maturing agent, Toxicology and applied Pharmacology 7, 445–472 (1965).

Three sound volunteers were treated for 30 days with 1500 mgr a day of a azobisformamide in three portions of 500 mgr.

No secondary effect was reported and the hematological parameters remained perfectly normal for the experimental treatment of 30 days.

On the other handy three patients presenting different stages of AIDS were also treated with azobisformamide in the same dosages as he sound volunteers.

The first patient in final phase presented at least 30 $T_4$ lymphocytes/mm$^3$, abundant diarrheas and a complete space-time disorientation.

The second patient in "ARC" phase presented a lymphocytar $T_4$ population of 190/ mm$^3$, in constant decrease, as well as occasional diarrheas and anal herpes.

The third patient was a sound seropositive, he had a population of 350 $T_4$ lymphocytes/mm$^3$ and he had no sign of pathology.

The first patient had on day 0 of the treatment 1850 white corpuscules including 17% of lymphocytes of which 5% presented the $T_4$ receptor (namely 24 cells). On day 30 of the treatment, the white corpuscules were in an amount of 2600 including 20% of lymphocytes of which 9% presented the $T_4$ receptor (namely 49 cells/mm$^3$)., which represented an improvement of 100%. On the other hand, the diarrhea has ended, the patient had recovered his possibility of coherent talking with his near relations, as well as a limited walking autonomy.

The second patient had on day 30 280 $T_4$ lymphocytes/ $mm^3$, the diarrhea had completely disappeared as well as the anal herpes.

The third patient has on day 30 440 $T_4$ lymphocytes/ $mm^3$.

These results, even if they concern a restricted sampling, are remarkable and surprising and they could in no way be expected by the ones skilled in the art.

EXAMPLE 13

Disinfectant effevescent tablet for 100 $cm^3$ of water.

| | |
|---|---|
| 1.1'-Azobisdimethylformamide | 33 mgr |
| Citric acid | 15 mgr |
| Tartaric acid | 17,5 mgr |
| NaH $CO_3$ | 37,5 mgr |
| Avicel PH $1C_2$ | 27 mgr |
| Lactose EFK | 45 mgr |
| For one tablet: | 175 mgr |

EXAMPLE 14

Disinfectant effervescent tablet, for 1000 $cm^3$ of water.

| | |
|---|---|
| 2.2-Azobismethylformamidine | 330 mgr |
| Citric acid | 150 mgr |
| Tartaric acid | 175 mgr |
| $NaHCO_3$ | 375 mgr |
| Avicel PH $IC_2$ | 180 mgr |
| Lactose EFK | 522.2 mgr |
| Sodium lauryl sulfate | 64 mgr |
| Aerosil 200 | 3.8 mgr |
| For one tablet: | 1800 mgr |

EXAMPLE 15

Tooth-paste

To 100 gr of a tooth-paste comprising 4% of ricinilate, 30 mgr of 1.1'-azobisfluoroformamidine (for 30 days) were added.

EXAMPLE 16

| Mouth-wash | |
|---|---|
| Sodium perfluorate | 8 gr |
| Borax | 32 gr |
| Sodium chloride | 20 gr |
| Sodium bicarbonate | 40 gr |
| 1.1'-azobisfluoroformamidine | 30 gr |
| Mint oil | 3 drops |
| 1 coffee spoonful in a lukewarm water cup. | |

EXAMPLE 17

| Cream | |
|---|---|
| 1.1'-Azobisformamide | 1 gr |
| Triethanolamine | 1 gr |
| Glycerol | 2.5 gr |
| White wax | 2.5 gr |
| Stearic acid | 6 gr |
| Almond oil | 7.5 gr |
| Lavender oil | 2 drops |
| Aqua conservans, ad | 50 gr FMS |
| for 50 gr of cream. | |

EXAMPLE 18

| Talc | |
|---|---|
| 1.1'-Azobisformamide | 2 gr |
| Lavender oil | 5 drops |
| Talc ad | 100 gr |
| for 100 gr of talc. | |

EXAMPLE 19

| Liquid soap | |
|---|---|
| 1-Monochloro-azobisformamidine | 3 gr |
| Potassium soap | 60 gr |
| Lavender oil | 10 drops |
| Antiseptic solution ad | 100 gr |
| for 100 gr of soap. | |

EXAMPLE 20

Toilet paper, hygienic bands and tampons, wadding and the like.

A powder to be sprayed was first prepared, the composition of which is for example as follows:

| | |
|---|---|
| 1.1'-Azobisdimethylformamide | 20 mgr |
| Bismuth sub-gallate | 50 gr |
| Zinc peroxide | 100 gr |
| Talc | 840 gr |
| for 1 kg of powder to be sprayed. | |

This powder which adheres to the fibers of the treated products was then sprayed in a usual way.

EXAMPLE 21

| Oil for preservative sheath | |
|---|---|
| Silicone oil | 100 gr |
| 1.1'-Azobisformamide | 1 gr |

The preservative sheaths are coated with the preparation as well as on the internal face as on the external one.

It has to be understood that the present invention is in no way limited to the hereinabove described embodiments and that many variants may be brought therein without departing from the scope of this invention.

Many other disinfectant of pharmaceutical compositions may be provided in addition to those given as Examples, by simply using the formulations such as used in general in the concerned fields, such as cleaning products, cosmetic compositions, pharmaceutical products and the like.

Discussion

I. First Type

The assays according to Examples 8b, 9b, 10b, 10c, 11b, and 11c of the present specification.

All these experiments comprise isolating free virus, exposing the virus to the active substance, and finally infecting healthy cells with the exposed virus.

The infectious power of HIV-1 is measured according to the well-known ELISA test technique. These tests are quantitative tests which consist of binding to the p24 protein of the HIV-1 a marker which absorbs light in a predetermined spectrum. The more virus that is present in the cellular lysates, the more the marker is present and the higher the optical density.

Moreover, an examination of the inoculated cells was carried out with a phase-contrast microscope. If the substance to examine is without action on the virus, the infected cells are binding to other cells and form giant multinuclear cells, called syncytia. If the substance is active against the virus, there is no syncytia.

Examples 10c and 11c disclose a more accurate method than the ELISA test for examining whether the inoculated cells contain HIV-1 at the end of the assay, i.e., the PCR-Method.

All these assays are conducted in order to demonstrate whether the virus shows an infectious power or not after a treatment with an active substance, i.e., whether the virus is able to multiply or not in the infected cells after the treatment. It is impossible to deduce therefrom if the virus has been destroyed or not, but it is possible to determine if the virus continues to replicate or not, in the cells.

II. Second Type

The assay according to Example 9c of the present application.

Example 9c discloses an assay conducted on previously infected cells in order to examine them after treatment with an active substance.

In example 9c, Molt-3 cells infected by HTLVIII-B are examined. The cellular mortality is measured by the usual method of exclusion by means of trypan blue.

It results from this assay that the mortality of the infected cells is doubled, with respect to the mortality of controls.

It is possible to deduce from this assay that the active substance has a selective toxicity against cells infected by HIV.

III. Third Type

EXAMPLE 22

A new assay was conducted by the AIDS laboratory of the REGA Institute for Medical Research of the Katholieke Universiteit of Leuven. This assay was performed in order to examine whether the active substance inhibits the replication of the retroviruses within infected cells.

1,1'-azobisformamide was purchased from Riedel de Haen and stored in a refrigerator (4°–8° C.) under light-protected conditions. Dilutions were prepared in order to obtain concentrations of 0.4 µg/ml, 2 µg/ml, 10 µg/ml, 50 µg/ml and 250 µg/ml.

Peripheral Blood Lymphocytes (PBLs) were freshly collected from a single donor. PBLs were activated by phytohemagglutinin at 2 µg/ml during 3 days, and then cultured in the presence of IL-2 for 1 week.

HIV-1 strain $III_B$/LAI was provided by R. C. Gallo (Popovic M. et al, Science 1984, 224:497–500). Stocks were obtained from the culture supernatants of HIV-1 infected cell lines (HUT 78/$III_B$/LAI).

The inhibitory effects of 1,1'-azobisformamide on the replication of strain $III_B$/LAI in PBLs were monitored by the detection of HIV-1 p24 core antigens. PBLs were incubated with an excess of strain $III_B$/LAI at 37° C. for 60 min. All cells were washed once with RPMI 1640 medium. Thereafter cells were plated at 1×10$^6$ cells per ml in the presence of various concentrations of the test compound. Seven days after plating PBLs, p24 antigens were detected by enzyme-linked immunosorbent assay (ELISA) (HIV-1 p24 Core Profile ELISA from Du Pont).

This method comprises measuring the concentration of the viral antigen p24 in the supernatant, i.e., the concentration of free viruses produced by replication of the viruses present in the infected cells. This measure is expressed as a measure of protection (see Table I below), where $$\text{Protection (\%)} = \left(1 - \frac{p24 \text{ Concentration with active substance}}{p24 \text{ concentration in the control}}\right) \times 100$$

TABLE I

Inhibition of HIV-1 replication in acutely infected PBLs by 1,1'-azobisformamide
Cell line: PBLs acutely infected with $III_B$/LAI

| Compound | Concentration µg/ml | Protection (%) |
|---|---|---|
| 1,1'azobisformamide | 0 | 0 |
| | 0.4 | 15.2 |
| | 2 | 45.8 |
| | 10 | 77.6 |
| | 50 | Toxic |
| | 250 | Toxic |
| | 2.47 | IC50 |

"Toxic" means that the cells are destroyed, which renders impossible the ELISA test. However, this toxicity is maybe the result of the selective toxicity of the active substance against the infected cells. This result could be a supplementary advantage of the active substance. In any case, from concentration of 10 µg/ml, the substance inhibits advantageously the replication of the viruses.

Discussion

From the three types of assays discussed immediately above, the main effects of the active substances according to the invention may be summarized as follows:

(1) First type of assay: inactivation of free viruses.

(2) Second type of assay: selective toxicity of the active substance against cells infected by the viruses.

(3) Third type of assay: inhibition of the replication of the viruses within infected cells.

EXAMPLE 23

An additional assay was conducted in order to verify whether the active substances are also active against other viruses than the retroviruses. The assay consists of investigating the ability of 1,1'-azobisformamide (ADA) to inactivate Vesicular Stomatitis Virus (VSV) in plain RMI tissue culture medium.

The active substance was obtained from Aldrich Chemical Co., as an orange powder. The material was dissolved in DMSO to obtain a final concentration of 20 mg/ml.

One ml of VSV was thawed at room temperature and a sample of 0.06 ml of VSV is added to 29.94 ml of RPMI 1640 to form a 1/500 dilution. This dilution was shaken during 10 minutes at approximately 70 rpm.

After agitation, an aliquot of 1 ml of the viral suspension was removed and kept at room temperature as the non-treated process control sample.

Aliquots from the VSV suspension were distributed to four 15 ml sterile tubes as shown in Table II, to which were added aliquots of the ADA/DMSO solution as shown in the table. The final concentrations of ADA in the viral medium are shown in Table II.

TABLE II

| Final concentrations of ADA in the VSV media | | | |
|---|---|---|---|
| Tube # | Volume of VSV suspension (in ml) | Volume of ADA/DMSO solution (in ml) | Concentration of ADA in VSV medium (in μg/ml) |
| 1 | 4.938 | 0.062 | 250 |
| 2 | 4.963 | 0.037 | 150 |
| 3 | 4.975 | 0.025 | 100 |
| 4 | 4.987 | 0.012 | 50 |

At 10, 60 and 1200 minutes after addition of the ADA solution to the viral suspension, 1 ml was sampled from each tube, 0.055 ml of which was added to the first well of a limiting dilution assay series, whereas the remainder was frozen immediately and stored.

The dilution assay consists in tenfold dilutions of the VSV medium placed into wells containing monolayers of VERO cells. After incubation, cells are evaluated for cytopathic effects by light microscopy. The assay consists of determining the dilution of VSV medium at which 50% of the wells to which the dilution has been added show surviving cells. This dilution, which inhibits cell death in half the wells, is called the TCID 50, and it is expressed as the logarithm of the dilution factor. Hence a TCID 50 corresponding to a dilution of the viral medium of 1/10,000 will be expressed as $\log_{10}$ 10,000 (dilution factor=10,000), i.e. 4.0. To compare the inhibitory effects of a protective compound on cell death with a non-treated control VSV medium, the difference between the TCID 50 of the viral medium with a given concentration of the compound and the TCID 50 of the viral medium without the compound (control) is used to express to the potency of the protective effect of the compound. This difference between the two TCID 50 values expressed in logarithms is called the "log reduction".

TCID 50 determinations were made on the process control sample and on the four tubes as described in table II, each at three different times after addition of ADA to the viral suspension (i.e. 10, 60, and 1200 min.). Log reductions are therefore available for each of the four ADA concentrations tested at each of the three time points.

Results

No toxicity against VERO cells was observed, even at the highest ADA/DMSO concentrations tested and after exposure of the cells during 20 hours.

The TCID 50 values and corresponding log reductions are presented in Table III.

TABLE III

| TCID 50 and Log reduction (log red) results | | | | | | |
|---|---|---|---|---|---|---|
| TIME POINT | END- | ADA CONCENTRATION (μg/ml) | | | | |
| (min) | POINT | 0 | 50 | 100 | 150 | 250 |
| 10 | TCID 50 | 7.95 | 6.90 | 6.73 | 6.73 | 6.55 |
| | Log Red | — | 1.05 | 1.22 | 1.22 | 1.40 |

TABLE III-continued

| TCID 50 and Log reduction (log red) results | | | | | | |
|---|---|---|---|---|---|---|
| TIME POINT | END- | ADA CONCENTRATION (μg/ml) | | | | |
| (min) | POINT | 0 | 50 | 100 | 150 | 250 |
| 60 | TCID 50 | 7.95 | 6.55 | 6.73 | 6.55 | 6.55 |
| | Log Red | — | 1.40 | 1.22 | 1.40 | 1.40 |
| 1200 | TCID 50 | 6.03 | 4.28 | 3.75 | 3.58 | 3.93 |
| | Log Red | — | 1.75 | 2.28 | 2.45 | 2.10 |

TCID 50 of control—TCID 50 of ADA treated sample= log reduction, i.e., for example 7.95–6.90=1.05.

The strongest effect with a log reduction of 2.28, 2.45 and 2.10 is observed after exposure at an ADA concentration of 150 μg/ml.

It can therefore be concluded that ADA dissolved in DMSO is effective against VSV in the foregoing type of VERO cell assay, with log reductions in excess of 2.0 at ADA concentrations of ≧100 μg/ml after a duration of exposure of between 1 and 20 hours.

EXAMPLE 24

Liquid media was provided wherein azobisformamide (ADA, also referred to as azodicarbonamide) was present in the liquid at a concentration of from 0.4 μgr/ml to 250.0 μgr/ml. The media was found to inhibit the replication of HIV-1 (strain IIIB(LAI)) and wild HIV-1 strains including strains phenotypically resistant to AZT (zidovudine), in Peripheral Blood Lymphocytes (PBLs) derived from HIV-1-negative human donors, and inhibits the replication of HIV-1 and HIV-2 (ROD) in MT4 cells.

Target cells were infected with HIV stock solution and cultured in the liquid media. After collection from donors, cells were separated using the Ficoll/Hypaque cell separation technique, and PBL's were washed twice in phosphate buffered saline. Target cells were cultured in the presence of phytohemagglutinin for three days at 37° C. in a $CO_2$-controlled incubator. This was followed by a 90 minute incubation in the presence of the viral solution. Non-absorbed virus was removed during 5 washing steps with fresh culture medium, and HIV-infected and mock-infected PBL's and MT4 cells were resuspended at $2\times10^5$ and $5\times10^5$ cells per ml, respectively, in complete medium (RPMI 1640 DM medium supplemented with 10% fetal calf serum and 20 μgr/ml gentamycin) supplemented with 5% recombinant interleukin 2, to which the liquid media was added in order to reach the desired final concentrations. Fresh medium without ADA was added at day 4 after infection of the target cells. HIV p24 antigen in the cell culture media was quantified 7 to 8 days after infection by an antigen-capture assay using a sandwich ELISA technique. The median IC50 (concentration in μgr/ml inhibiting viral replication by 50%) was found to be 8 μgr/ml calculated from an IC50 range of from 1.6 μgr/ml to 14.8 μgr/ml as shown in the Table below. Complete inhibition (≧90% inhibition, also referred to as IC90) was achieved with wild strains from patients, at a median concentration of 18 μgr/ml, calculated from the range of 17.4 μgr/ml to 21.2 μgr/ml as shown in Table IV below. Individual test results are also summarized in the Table below. From Table IV, it can be seen that the lowest observed IC50 value is 1.6 μgr/ml in MT4 cells infected with HIV-1 strain LAI/IIIB.

TABLE IV

| TYPE | STRAIN | PBL's Exp. # | PBL's IC50 | PBL's IC90 | MT4 CELLS Exp. # | MT4 CELLS IC50 | MT4 CELLS IC90 |
|---|---|---|---|---|---|---|---|
| HIV-1 | LAI/ | 1 | 2.5 | >10.0 | 13 | 4.5 | >25.5 |
|  | IIIB | 2 | 7.0 | 47.0 | 14 | 9.9 | >15.7 |
|  |  | 3 | 13.8 | 39.7 | 15 | 9.7 | 12.7 |
|  |  | 4 | 3.2 | 35.0 | 16 | 14.8 | >31.1 |
|  |  | 5 | 3.9 | >10.0 | 17 | 1.6 | 8.0 |
|  |  |  |  |  | 18 | 5.1 | 8.0 |
|  | Wild A* | 6 | 8.9 | 17.4 |  |  |  |
|  | Wild B* | 7 | 11.6 | 18.6 |  |  |  |
|  | Wild C* | 9 | 11.1 | 18.0 |  |  |  |
|  | Wild D | 9 | 10.0 | 18.1 |  |  |  |
|  | Wild E | 10 | 8.3 | 18.4 |  |  |  |
|  | Wild F* | 11 | 6.4 | 19.0 |  |  |  |
|  | Wild G* | 12 | 11.2 | 21.2 |  |  |  |
| HIV-2 | ROD |  |  |  | 19 | 4.1 | 7.6 |
|  |  |  |  |  | 20 | 6.0 | >29.0 |
|  |  |  |  |  | 21 | 14.3 | >17.5 |
|  |  |  |  |  | 22 | 6.7 | 8.3 |

*Phenotypically resistant to AZT; wild strains F and G are also syncytium inducers.

EXAMPLE 25

Pharmaceutical grade ADA in gelatin capsules or enteric-coated tablets, each containing 500 mg, was administered as single oral doses to healthy volunteers in order to estimate the maximum tolerated dose (MTD) in humans and to detect urinary excretion of ADA. Enteric-coated tablets are generally considered as having a delayed distribution in the gastro-enteric tractus. Doses of 35 mg/kg (mgADA per kg body weight), 70 mg/kg, and 140 mg/kg were administered. No adverse effects such as changes in hemodynamic parameters or subjective well-being were observed with the lower doses, whereas a flu-like syndrome was observed from 6 hours after intake of the highest dose. The flu-like symptoms lasted several hours. The MTD for a single dose was therefore estimated to be 140 mg/kg. In the urine collected 2 to 3 hours after intake of a single dose of 3 g (6 gelatin capsules≈35 mg/kg), ADA was detected in the urine of one volunteer at a concentration of 25–30 µgr/ml, showing that the drug can be absorbed and even excreted in its active form.

EXAMPLE 26

Pharmaceutical grade ADA in gelatin capsules, each containing 500 mg, was administered as single oral doses to healthy volunteers to determine its tolerability and safety. A dose-related increase in methemoglobin was observed in one volunteer, with Cmax at 1–1.5 hours after intake. Methemoglobin returned to normal within half an hour. Glutathione and methemoglobin reduces in peripheral blood were slightly depressed in the volunteers from doses of 40 mg/kg. These changes were reversible within 4–6 hours from intake. No adverse effects were observed after either 40 mg/kg or 60 mg/kg doses on a broad range of hematological and chemical parameters in the blood and urine of the volunteers. No adverse effects were observed at any of the tested dosages on blood pressure, pulse, or respiratory rate. It is therefore concluded that (1) ADA is absorbed via the gastro-intestinal route, (2) ADA distributes readily to intracellular compartments, with an intracellular peak 1–1.5 hours after intake, and (3) ADA is well tolerated at single oral dosages of up to 60 mg per kg body weight.

EXAMPLE 27

Pharmaceutical grade ADA in gelatin capsules, containing 250 mg or 500 mg, were administered to one patient with stage IV AIDS. The patient started ADA treatment with a 500 mg dose three times a day corresponding to a total of about 25 mg/kg body weight taken three times a day. The total daily dose was therefore 1.5 gram. Absolute CD4 lymphocyte counts increased from 77 cells/mm$^3$ to 144 cells/mm$^3$ over a 26-week period. Concomitant medication with DDI (didanosine, from Bristol Myers Squibb), and subsequently with a combination of DDI and DDC (zalcitabine, from Hoffman-LaRoche) was stopped because of resistance, and another experimental reverse-transcriptase (RT) inhibitor (d4T from Bristol-Meyers Squibb) was administered instead. As CD4 lymphocyte counts continued to improve, ADA was voluntarily withdrawn in order to test the effect on CD4 lymphocyte counts. Under RT medication, but without ADA, the CD4 lymphocyte count returned to baseline within two months, the patient lost weight and developed intractable diarrhea requiring rehydration. ADA was restarted at a dose of 1 gram three times a day, twice the initial dose, whereupon the CD4 lymphocyte count returned to 144 cells/mm$^3$ within two weeks. The patient gained considerable weight and was free of diarrhea 12 weeks after restarting ADA. Fifteen weeks after restarting ADA, the CD4 lymphocyte count increased further to 190 cells/mm$^3$. No adverse effects that could be drug-related were reported, despite occasional dosage increases of up to 2 grams three times a day. Gene sequencing based on viral RNA-extraction from the patient's blood shows that this strain has mutations in codons 67, 70, 184, 215 and 219, indicating that it is genetically resistant to AZT, DDI, DDC, and 3TC (lamivudine available from BioChem Pharma/Glaxo).

EXAMPLE 28

ADA in a liquid medium was tested in an acellular in-vitro system for any inhibitory effect on HIV-1 reverse transcriptase (RT) using the polyrC-oligodG template-primer-complex. ADA is not an RT-inhibitor at concentrations up to the IC90. From concentrations of 60 µgr/ml upward, there is a 50% inhibition of RT. ADA is not a Tat-antagonist. ADA does not inhibit pepsin, an enzyme with an active site almost identical to that of HIV-1 protease. Therefore, ADA inhibits HIV replication with an as yet unknown but original mode of action. In-vitro, ADA showed additive effects to those of didanosine at concentrations at and below the IC50.

EXAMPLE 29

Four patients with advanced AIDS have been treated with ADA. One patient has been treated during two periods, i.e., treated was restarted after a return to baseline subsequent to the withdrawal of ADA. The patients received capsules containing 500 mg. The dosage regimen was 500 mg three times a day except during the second treatment period in the patient who is also the patient of Example 27 where the dosage regimen was increased to 1 gram three times a day. The graph represents the median value of all CD4 lymphocyte counts measured in the patients. All dosage regimens are combined. There were five periods of ADA treatment. Due to the small number of values, medians were calculated by carrying forward the last values of the patients with no data point in the corresponding treatment week. Values of patients who dropped out of the study were carried forward. The linear regression is represented by the equation Y=77.2 +4.8 X, where Y is the absolute CD4 count/ml and X is the number of weeks after start of ADA treatment. The correlation coefficient is 0.79.

Although the present invention has been described in connection with preferred embodiments, it will be appreciated by those skilled in the art that additions, modifications, substitutions and deletions not specifically described may be made without departing from the spirit and scope of the invention defined in the appended claims.

What is claimed is:

1. A composition comprising:

an active substance selected from one or more azoic compound of the general formula

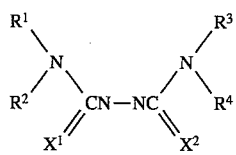

wherein $R^1$, $R^2$, $R^3$ and $R^4$ are identical or different and each represents an atom of hydrogen or an aliphatic or aromatic hydrocarbon radical comprising from 1 to 6 carbon atoms, $R^1$ and $R^2$ may be bonded together to form a heterocyclic ring with their adjacent nitrogen atom, and $R^3$ and $R^4$ may be bonded together to form a heterocyclic ring with their adjacent nitrogen atom; $X^1$ and $X^2$ are identical or different and each represents an oxygen atom or an $NR^5$ group, wherein $R^5$ is a hydrogen atom, an aliphatic or aromatic hydrocarbon radical comprising from 1 to 6 carbon atoms, or a nitro group; and wherein when two $NR^5$ groups are simultaneously present each $R^5$ may be identical to or different from the other; and a liquid medium, wherein said active substance is present in said liquid medium at a concentration of from 1.6 μgr/ml to 2 mgr/ml.

2. A composition as defined in claim 1, wherein said active substance comprises at least one member selected from the group consisting of 1,1'-azobisformamide and 1,1'-(azodicarbonyl)dipiperidine.

3. A composition as defined in claim 1, wherein said active substance is azobisformamide.

4. A composition as defined in claim 1, wherein said liquid medium comprises a mouthwash composition.

5. A composition as defined in claim 1, wherein said liquid medium comprises a liquid soap composition.

6. A composition as defined in claim 1, wherein said liquid medium comprises a skin cream composition.

7. A composition as defined in claim 1, wherein said liquid medium comprises a lubricating oil composition.

8. A composition as defined in claim 1, wherein said liquid medium comprises at least one member selected from the group consisting of pharmaceutically compatible excipients, adjuvants and carriers.

9. A tablet comprising a composition, said composition comprising an active substance selected from one or more azoic compound of the general formula

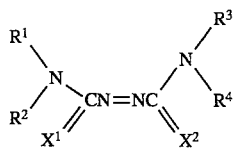

wherein $R^1 R^2 R^3$ and $R^4$ are identical or different and each represents an atom of hydrogen or an aliphatic or aromatic hydrocarbon radical comprising from 1 to 6 carbon atoms, $R^1$ and $R^2$ may be bonded together to form a heterocyclic ring with their adjacent nitrogen atom, and $R^3$ and $R^4$ may be bonded together to form a heterocyclic ring with their adjacent nitrogen atom; $X^1$ and $X^2$ are identical or different and each represents an oxygen atom or an $NR^5$ group, wherein $R^5$ is a hydrogen atom, an aliphatic or aromatic hydrocarbon radical comprising from 1 to 6 carbon atoms, or a nitro group; and wherein when two $NR^5$ groups are simultaneously present each $R^5$ may be identical to or different from the other.

10. A tablet as defined in claim 9, further comprising at least one member selected from the group consisting of pharmaceutically compatible excipients, adjuvants and carriers.

11. A tablet as defined in claim 9, further comprising an effervescent agent.

12. In combination, a capsule and a composition within said capsule, said composition comprising an active substance selected from one or more azoic compound of the general formula.

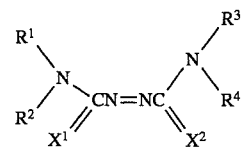

wherein $R^1$, $R^2$, $R^3$ and $R^4$ are identical or different and each represents an atom of hydrogen or an aliphatic or aromatic hydrocarbon radical comprising from 1 to 6 carbon atoms, $R^1$ and $R^2$ may be bonded together to form a heterocyclic ring with their adjacent nitrogen atom, and $R^3$ and $R^4$ may be bonded together to form a heterocyclic ring with their adjacent nitrogen atom; $X^1$ and $X^2$ are identical or different and each represents an oxygen atom or an $NR^5$ group, wherein $R^5$ is a hydrogen atom, an aliphatic or aromatic hydrocarbon radical comprising from 1 to 6 carbon atoms, or a nitro group; and wherein when two $NR^5$ groups are simultaneously present each $R^5$ may be identical to or different from the other.

13. A suppository comprising an active substance selected from one or more azoic compound of the general formula

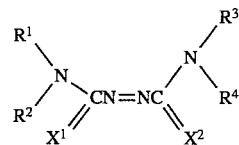

wherein $R^1$, $R^2$, $R^3$ and $R^4$ are identical or different and each represents an atom of hydrogen or an aliphatic or aromatic hydrocarbon radical comprising from 1 to 6 carbon atoms, $R^1$ and $R^2$ may be bonded together to form a heterocyclic ring with their adjacent nitrogen atom, and $R^3$ and $R^4$ may be bonded together to form a heterocyclic ring with their adjacent nitrogen atom; $X^1$ and $X^2$ are identical or different and each represents an oxygen atom or an $NR^5$ group, wherein $R^5$ is a hydrogen atom, an aliphatic or aromatic hydrocarbon radical comprising from 1 to 6 carbon atoms, or a nitro group; and wherein when two $NR^5$ groups are simultaneously present each $R^5$ may be identical to or different from the other.

14. A powder composition comprising talc and an active substance selected from one or more azoic compound of the general formula

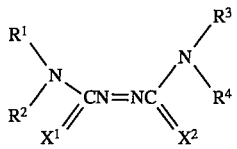

wherein $R^1$, $R^2$, $R^3$ and $R^4$ are identical or different and each represents an atom of hydrogen or an aliphatic or aromatic hydrocarbon radical comprising from 1 to 6 carbon atoms, $R^1$ and $R^2$ may be bonded together to form a heterocyclic ring with their adjacent nitrogen atom, and $R^3$ and $R^4$ may be bonded together to form a heterocyclic ring with their adjacent nitrogen atom; $X^1$ and $X^2$ are identical or different and each represents an oxygen atom or an $NR^5$ group, wherein $R^5$ is a hydrogen atom, an aliphatic or aromatic hydrocarbon radical comprising from 1 to 6 carbon atoms, or a nitro group; and wherein when two $NR^5$ groups are simultaneously present each $R^5$ may be identical to or different from the other.

15. A powder as defined in claim 14, wherein said active substance is present in said composition at a concentration of at least about two percent by weight.

16. A method of treating a human or other animal infected with a virus of the retrovirus group, said method comprising the step of administering a therapentically effective amount of an active substance to a human or other animal infected with a virus of the retrovirus group, said active substance being selected from one or more azoic compound of the general formula

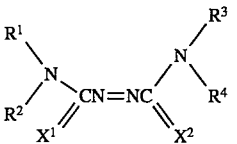

wherein $R^1$, $R^2$, $R^3$ and $R^4$ are identical or different and each represents an atom of hydrogen or an aliphatic or aromatic hydrocarbon radical comprising from 1 to 6 carbon atoms, $R^1$ and $R^2$ may be bonded together to form a heterocyclic ring with their adjacent nitrogen atom, and $R^3$ and $R^4$ may be bonded together to form a heterocyclic ring with their adjacent nitrogen atom; $X^1$ and $X^2$ are identical or different and each represents an oxygen atom or an $NR^5$ group, wherein $R^5$ is a hydrogen atom, an aliphatic or aromatic hydrocarbon radical comprising from 1 to 6 carbon atoms, or a nitro group; and wherein when two $NR^5$ groups are simultaneously present each $R^5$ may be identical to or different from the other.

17. A method as in claim 16, wherein said active substance is orally administered in the form of a tablet.

18. A method as in claim 16, wherein said active substance is orally administered in the form of a capsule.

19. A method as in claim 16, wherein said active substance is orally administered in the form of a caplet.

20. A method as in claim 16, wherein said active substance is orally administered in the form of a gelatin capsule.

21. A method as in claim 16, wherein said active substance is orally administered in the form of an enteric-coated tablet.

22. A method as in claim 16, wherein said active substance is administered in said amount at least one time per day for more than one day.

23. A method as in claim 16, wherein said active substance is administered in said amount three times per day for more than one day.

24. A method as in claim 16, wherein said active substance is administered in the form of a suppository.

25. A method as in claim 16, wherein said active substance is administered in the form of an injectable.

26. A method as in claim 16, wherein said human or other animal has a body weight measured in kilograms and said amount is equal to between 7 milligram and 140 milligram active substance per kilogram of said body weight and is administered only one time a day for more than one day.

27. A method as in claim 16, wherein said human or other animal has a body weight measured in kilograms and said amount is equal to between 20 milligram and 90 milligram active substance per kilogram of said body weight and is administered three times a day for more than one day.

28. A method as in claim 16, wherein said active substance is azobisformamide.

* * * * *

UNITED STATES PATENT AND TRADEMARK OFFICE
CERTIFICATE OF CORRECTION

PATENT NO.   : 5,585,367
DATED        : December 17, 1996
INVENTOR(S)  : Michel Vandevelde et al.

It is certified that error appears in the above-indentified patent and that said Letters Patent is hereby corrected as shown below:

In the Abstract, line 4, correct the formula to:

Col. 21:

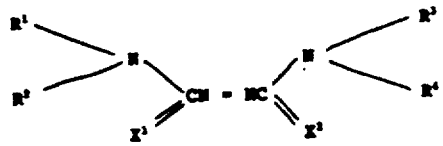

In claim 1, line 4, correct the formula to:

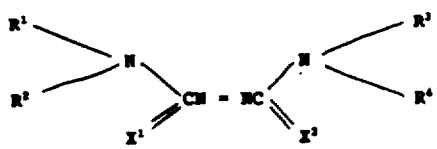

Signed and Sealed this

Twelfth Day of August, 1997

Attest:

BRUCE LEHMAN

Attesting Officer

Commissioner of Patents and Trademarks